United States Patent
Stone et al.

(10) Patent No.: US 11,684,266 B2
(45) Date of Patent: Jun. 27, 2023

(54) PROBE FOR OPTICAL SPECTROSCOPY

(71) Applicants: The University of Bristol, Bristol (GB); The University of Exeter, Devon (GB); Gloucestershire Hospitals NHS Foundation Trust, Gloucestershire (GB)

(72) Inventors: Nicholas Stone, Devon (GB); John Charles Clifford Day, Bristol (GB)

(73) Assignees: The University of Bristol, Bristol (GB); The University of Exeter, Devon (GB); Gloucestershire Hospitals NHS Foundation Trust, Gloucestershire (GB)

( * ) Notice: Subject to any disclaimer, the term of this patent is extended or adjusted under 35 U.S.C. 154(b) by 867 days.

(21) Appl. No.: 16/495,560

(22) PCT Filed: Mar. 15, 2018

(86) PCT No.: PCT/GB2018/050678
§ 371 (c)(1),
(2) Date: Sep. 19, 2019

(87) PCT Pub. No.: WO2018/172746
PCT Pub. Date: Sep. 27, 2018

(65) Prior Publication Data
US 2020/0015684 A1 Jan. 16, 2020

(30) Foreign Application Priority Data
Mar. 20, 2017 (GB) ...................................... 1704405

(51) Int. Cl.
*A61B 5/00* (2006.01)
*G02B 6/40* (2006.01)

(52) U.S. Cl.
CPC .......... *A61B 5/0075* (2013.01); *A61B 5/0084* (2013.01); *A61B 5/0086* (2013.01);
(Continued)

(58) Field of Classification Search
CPC ................ A61B 5/0075; A61B 5/6848; A61B 2562/228
See application file for complete search history.

(56) References Cited

U.S. PATENT DOCUMENTS 5,219,345 A 6/1993 Potter
5,769,791 A 6/1998 Benaron et al.
(Continued)

FOREIGN PATENT DOCUMENTS

JP 2015166818 A 9/2015
WO 9214399 A1 9/1992
(Continued)

OTHER PUBLICATIONS

Utzinger et al., "Fiberoptic Probes for Biomedical Optical Spectroscopy" Journal of Biomedical Optics 8(1), 121-147, Jan. 2003 (Year: 2003).*
(Continued)

*Primary Examiner* — Colin T. Sakamoto
(74) *Attorney, Agent, or Firm* — Hunton Andrews Kurth LLP

(57) ABSTRACT

A probe comprising a body portion and a tip portion. The body portion comprises: a first mounting portion comprising a plurality of first carriers, each first carrier being arranged to support an elongate first waveguide, the first carriers being disposed in an equiangular arrangement around a longitudinal axis of the body portion; a plurality of first waveguides, each first waveguide being supported in a respective one of the plurality of first carriers; and a body end fitting at which first ends of the first waveguides are
(Continued)

supported in the equiangular arrangement around the longitudinal axis of the body portion such that the first waveguides can transmit electromagnetic radiation signals from an energy source to the body end fitting and/or transmit electromagnetic radiation signals from the body end fitting to a receiver. The tip portion comprises: a second mounting portion comprising a plurality of second carriers, each second carrier being arranged to support an elongate second waveguides, the second carriers being disposed in the equiangular arrangement around a longitudinal axis of the tip portion; a plurality of second waveguides, each second waveguides being supported in a respective one of the plurality of second carriers; and a tip end fitting at which first ends of the second waveguides are supported in the equiangular arrangement around the longitudinal axis of the tip portion; and an elongate conduit for piercing human tissue.

16 Claims, 6 Drawing Sheets

(52) U.S. Cl.
CPC .... *A61B 5/6848* (2013.01); *A61B 2560/0443* (2013.01); *A61B 2562/228* (2013.01); *G02B 6/403* (2013.01)

(56) References Cited

U.S. PATENT DOCUMENTS

| | | |
|---|---|---|
| 6,208,887 B1 | 3/2001 | Clarke |
| 2004/0073120 A1 | 4/2004 | Motz et al. |
| 2006/0264745 A1 | 11/2006 | Da Silva |
| 2007/0239033 A1* | 10/2007 | Tearney ............... G01N 21/23 600/407 |
| 2010/0094109 A1 | 4/2010 | Tang |
| 2012/0243830 A1 | 9/2012 | Rondeau et al. |
| 2014/0003779 A1 | 1/2014 | Arakawa et al. |
| 2016/0252683 A1 | 9/2016 | Sasaki et al. |
| 2019/0388069 A1* | 12/2019 | Weber ............... A61B 5/6848 |

FOREIGN PATENT DOCUMENTS

| | | |
|---|---|---|
| WO | 0019889 A1 | 4/2000 |
| WO | 2013064804 A1 | 5/2013 |
| WO | WO 2013/064804 | 5/2013 |

OTHER PUBLICATIONS

International Searching Authority, PCT International Search Report and Written Opinion, International Application No. PCT/GB2018/050678, dated Jul. 3, 2018, pp. 1-14.

United Kingdom Intellectual Property Office, United Kingdom Patent Application No. GB1704405.8, Combined Search and Examination Report Under Sections 17 and 18(3), dated Sep. 18, 2017, pp. 1-9.

European Patent Office, International Application No. PCT/GB2018/050678, PCT International Search Report and Written Opinion of the International Searching Authority, dated Jul. 3, 2018, pp. 1-14.

European Patent Office, European Patent Application No. 18714045.4, Communication Pursuant to Article 94(3) EPC, dated Mar. 24, 2023, pp. 1-6.

* cited by examiner

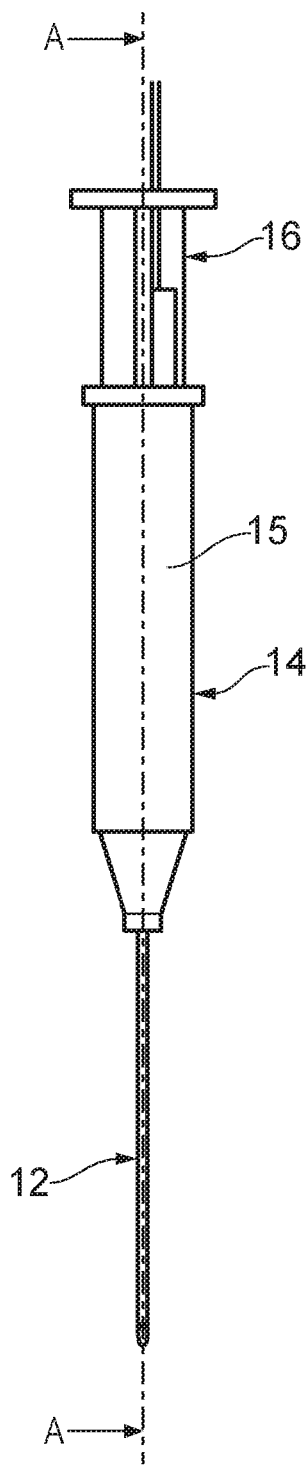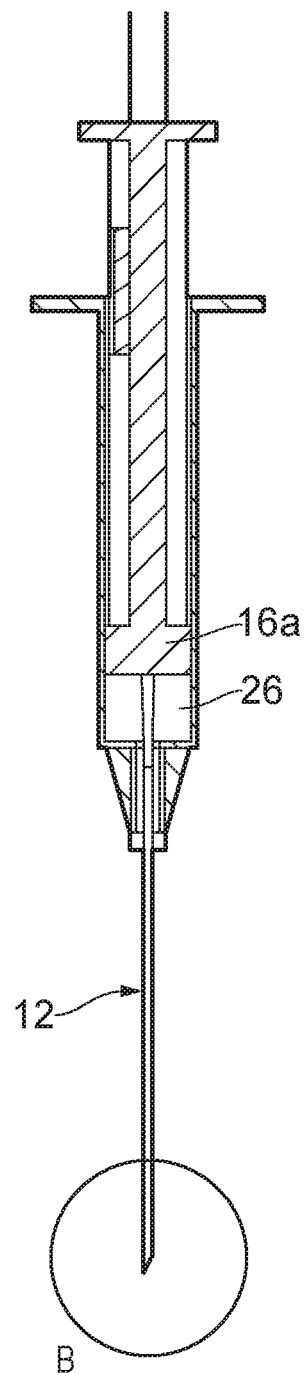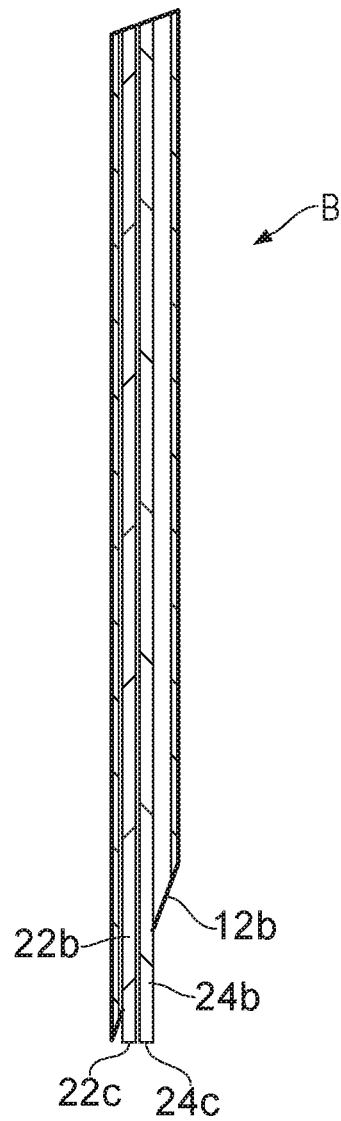
FIG. 2a
FIG. 2b
FIG. 2c

PROBE FOR OPTICAL SPECTROSCOPY

This application is a U.S. national phase application under 35 U.S.C. § 371 of International Application No. PCT/GB2018/050678, filed Mar. 15, 2018, which claims priority to U.K. Application No. 1704405.8, filed Mar. 20, 2017, the complete disclosures of which are incorporated herein by reference.

BACKGROUND

During medical examination of a tissue sample it can be beneficial to identify the tissue type and/or disease state thereof.

For example, when cancer is suspected, a patient may have a tumour removed or biopsied and sent for histopathology analyses. Conventional handling involves the tissue undergoing fixation, staining with dyes, mounting and then examination under a microscope for analysis. Typically, the time taken to prepare the specimen is of the order of one day. The pathologist will view the sample and classify the tissue as malignant or benign based on the shape, colour and other cell and tissue characteristics. The result of this manual analysis depends on the choice of stain, the quality of the tissue processing and staining, and ultimately on the quality of education, experience and expertise of the specific pathologist.

Probes have been devised which contain optical fibres to enable testing of subcutaneous tissue and/or fluid.

However, the present inventors have identified that known probes can be time consuming and/or expensive to manufacture.

SUMMARY

By way of a non-limiting overview, embodiments of the invention relate to a probe in which a body portion positions free ends of first waveguides in an equal angular spacing around the axis of the body, and a tip portion positions free ends of second waveguides in the same equal angular spacing around the axis of the tip portion. Thus, during manufacture of the tip, this enables the second waveguides to be randomly mounted in the second mounting portion and subsequently the second mounting portion can be rotated about its axis to align a particular one of the second waveguides with a particular one of the first waveguides. This can simply manufacture of the tip portion, reducing both time and cost.

According to a first aspect of the invention, there is provided a probe, the probe comprising:
 a body portion, the body portion comprising:
  a first mounting portion comprising a plurality of first carriers, each first carrier being arranged to support an elongate first waveguide, the first carriers being disposed in an equiangular arrangement around a longitudinal axis of the body portion;
  a plurality of first waveguides, each first waveguide being supported in a respective one of the plurality of first carriers; and
  a body end fitting at which first ends of the first waveguides are supported in the equiangular arrangement around the longitudinal axis of the body portion such that the first waveguides can transmit electromagnetic radiation signals from an energy source to the body end fitting and/or transmit electromagnetic radiation signals from the body end fitting to a receiver; and
 a tip portion arranged to be removably coupled to the body portion in a coaxial manner by one of more connectors, the tip portion comprising:
  a second mounting portion comprising a plurality of second carriers, each second carrier being arranged to support an elongate second waveguide, the second carriers being disposed in the equiangular arrangement around a longitudinal axis of the tip portion;
  a plurality of second waveguides, each second waveguides being supported in a respective one of the plurality of second carriers;
  a tip end fitting at which first ends of the second waveguides are supported in the equiangular arrangement around the longitudinal axis of the tip portion; and
  an elongate conduit for piercing human tissue, the elongate conduit having a first opening and a second opening, the first opening being coupled (directly or indirectly) to the second mounting portion with the second waveguides extending from the second mounting portion into the elongate conduit such that, when the tip portion is coupled to the body portion and the first waveguides are axially aligned with the second waveguides, the second waveguides can transmit electromagnetic radiation signals from the first waveguides to the second opening of the elongate conduit and/or transmit electromagnetic radiation signals from the second opening of the elongate conduit to the first waveguides.

Thus, a probe according to this aspect includes a conduit, such as a needle, via which electromagnetic radiation can be used for examining a tissue sample. The conduit is arranged and configured such that it may easily be inserted into human tissue and as such the probe can be used to test subcutaneous tissue and/or fluid. The probe can be coupled to a receiver that can be used to analyse the electromagnetic radiation returned from the sample through the conduit. The tip portion, which includes the elongate conduit and in use is likely to be contaminated by test tissue or test fluid, can be uncoupled from the body portion of the probe. As such, the tip portion can be discarded following a single use, but the body portion can be retained for subsequent use. Advantageously, the body portion mounting portion positions the free ends of the first waveguides in an equal angular spacing around the axis of the body; the tip portion mounting portion positions the free ends of the second waveguides in the same equal angular spacing around the axis of the tip portion. Thus, during manufacture of the tip, this enables the second waveguides to be randomly mounted in the second mounting portion and subsequently the second mounting portion can be rotated about its axis to align a particular one of the second waveguides with a particular one of the first waveguides. This can simply manufacture of the tip portion, reducing both time and cost.

According to a second aspect of the invention, there is provided a tip portion of a probe arranged to be removably coupled to a body portion in a coaxial manner by one of more connectors, the body portion comprising: a first mounting portion comprising a plurality of first carriers, each first carrier being arranged to support an elongate first waveguide, the first carriers being disposed in an equiangular arrangement around a longitudinal axis of the body portion; a plurality of first waveguides, each first waveguide being supported in a respective one of the plurality of first carriers; and a body end fitting at which first ends of the first waveguides are supported in the equiangular arrangement around the longitudinal axis of the body portion such that the first waveguides can transmit electromagnetic radiation signals from an energy source to the body end fitting and/or transmit electromagnetic radiation signals from the body end fitting to a receiver, the tip portion comprising:
- a second mounting portion comprising a plurality of second carriers, each second carrier being arranged to support an elongate second waveguides, the second carriers being disposed in the equiangular arrangement around a longitudinal axis of the tip portion;
- a plurality of second waveguides, each second waveguide being supported in a respective one of the plurality of second carriers;
- a tip end fitting at which first ends of the second waveguides are supported in the equiangular arrangement around the longitudinal axis of the tip portion; and
- an elongate conduit for piercing human tissue, the elongate conduit having a first opening and a second opening, the first opening being coupled (directly or indirectly) to the second mounting portion with the second waveguides extending from the second mounting portion into the elongate conduit such that, when the tip portion is coupled to the body portion and the first waveguides are axially aligned with the second waveguides, the second waveguides can transmit electromagnetic radiation signals from the first waveguides to the second opening of the elongate conduit and/or transmit electromagnetic radiation signals from the second opening of the elongate conduit to the first waveguides.

The following are options features of the first and second aspects.

The particular one of the first waveguides can be a first excitation waveguide arranged to transmit electromagnetic radiation signals from the energy source to the body end fitting.

The particular one of the second waveguides can be a second excitation waveguide arranged to transmit electromagnetic radiation signals from the first excitation waveguide to the second opening of the elongate conduit.

The remaining ones of the first and second waveguides can be collection waveguides. The second collection waveguides can each be arranged to transmit electromagnetic radiation signals from the second opening of the elongate conduit to the ends of the first collection waveguides at the body end fitting. The first collection waveguides can each be arranged to transmit electromagnetic radiation signals from the body end fitting to the receiver.

The tip portion and body portion can each define a cooperating keying formation arranged to permit the tip portion to be coupled to the body portion in just a single configuration.

The second mounting portion and the tip end fitting can be discrete portions of the tip that are coupled together during manufacture after the second mounting portion has been rotated about its axis to align the particular one of the second waveguides with the particular one of the first waveguides.

The tip portion can comprise at least four, more preferably at least five, and even more preferably at least seven second waveguides, the diameter of each second waveguide being such that the second ends of the second waveguides are housed within the bore of the elongate conduit in a configuration in which the second excitation waveguide is central and surrounded by the second collection waveguides. The body portion can comprise an equal number of first waveguides.

The first mounting portion can be integrally formed with or can define the body end fitting.

Each waveguide can comprise optical fibre.

The conduit can comprise a hypodermic needle.

The energy source can comprise a light source, such as a laser.

The electromagnetic radiation can be within the range of ultraviolet to infrared.

In any embodiment of the invention including optical fibre, the fibre core can have a diameter of 300 μm or less, preferably 200 μm or less, and advantageously 150 μm or less.

The receiver can comprise a spectroscopic detector, such as a detector arranged to detect Raman spectra.

The body portion can house wave manipulation modules including lenses and filters. Thus, relatively expensive components of the probe such as the wave manipulation modules may be associated with the reusable portion of the probe.

In some embodiments, the tip portion does not comprise the elongate conduit.

According to a third aspect of the invention, there is provided an optical spectroscope including a probe according to the first aspect. The optical spectroscope may comprise a Raman or fluorescence spectroscope.

According to a fourth aspect of the invention, there is provided a method of assembling a tip portion of a probe according to the first aspect, the method comprising the steps of:
- providing a tip portion comprising a second mounting portion, a tip end fitting and an elongate conduit, the second mounting portion comprising a plurality of second carriers, each second carrier being arranged to support an elongate second waveguide, the second carriers being disposed in an equiangular arrangement around a longitudinal axis of the tip portion;
- mounting a plurality of second waveguides in the second mounting portion, each second waveguide being supported in a respective one of the plurality of second carriers such that first ends of the second waveguides are supported in the equiangular arrangement around the longitudinal axis of the tip portion at a tip end fitting and second ends of the second waveguides extend from the second mounting portion into a first opening of the elongate conduit;
- rotating the second mounting portion, such as around the longitudinal axis of the tip portion, to align a particular one of the second waveguides with a target position on the tip end fitting corresponding to the position of a first waveguide of a body portion such that, when the tip portion is coupled to the body portion and the second waveguides are axially aligned with the first waveguides, the second waveguides can transmit electromagnetic radiation signals from the first waveguides to the second opening of the elongate conduit and/or transmit electromagnetic radiation signals from the second opening of the elongate conduit to the first waveguides; and
- coupling the second mounting portion to the second interface surface to inhibit further relative rotation between them about the axis of the tip portion.

Optional features of the first and second aspects can be applied to the fourth aspect in an analogous manner.

BRIEF DESCRIPTION OF THE DRAWINGS

Embodiments of the invention will now be described with reference to the accompanying drawings, in which:

FIG. 1b is a diagram in cross section through A-A of the probe of FIG. 1a;

FIG. 2a is a diagram of the probe of FIG. 1a showing the second waveguides in a deployed condition;

FIG. 2b is a view in cross section through A-A of the probe of FIG. 2a;

FIG. 2c is an enlarged view of the tip region B of the probe of FIG. 2b;

FIG. 3 is a diagram of the optical coupling of the probe of FIG. 1a;

DETAILED DESCRIPTION

Figure 1A:
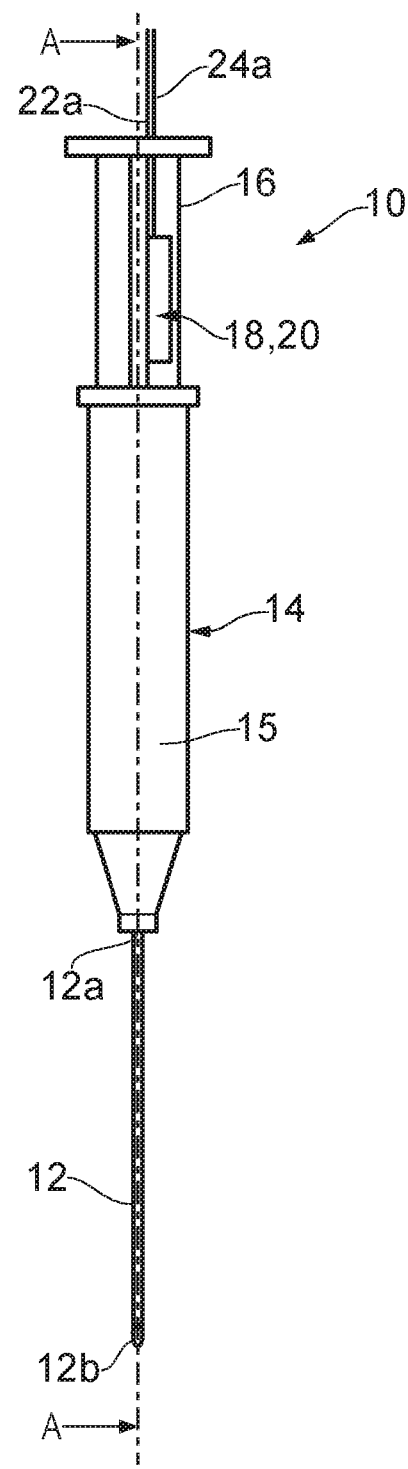
FIG. 1a is a diagram of a probe according to a first embodiment of the invention, showing the second waveguides in a retracted condition.

FIG. 1 shows a probe 10 according to a first embodiment of the present invention. The term "probe" is used in relation to embodiments of the invention to mean an instrument, such as a surgical instrument, which is suitable for, or arranged to be, at least partially inserted into human or animal tissue to enable a fluid or tissue sample to be tested in situ using electromagnetic radiation such as light.

The probe 10 according to embodiments of the invention enables subcutaneous tissue to be tested using spectroscopy, preferably Raman spectroscopy. As will be understood, when exciting optical energy of a single wavelength interacts with a molecule, the optical energy scattered by the molecule may contain small amounts of optical energy having wavelengths different from that of the incident exciting optical energy. This is known as the Raman effect. The wavelengths present in the scattered optical energy are characteristic of the structure of the molecule, and the intensity of this optical energy is dependent on the concentration of these molecules. Thus, the identities and concentrations of various molecules in a substance can be determined by illuminating the substance with energy of a single wavelength and then measuring the individual wavelengths, and their intensities, in the scattered optical energy. Raman spectroscopy provides a means for obtaining similar molecular vibrational spectra over optical fibres using visible or near infrared light that is transmitted by the optical fibres without significant absorption losses. In Raman spectroscopy, monochromatic light is directed to a sample and the spectrum of the light scattered from the sample is determined. It should however be noted that a probe according to embodiments of the invention may be used with any suitable receiver or detector, such as a spectroscopic detector arranged to measure fluorescence or elastic scattering.

The probe 10 generally comprises an elongate conduit 12 which is arranged to pierce human tissue, a two part wave coupling 18, 20, 22a, 22b, 24a, 24b arranged to transmit electromagnetic radiation from an energy source (not shown) into the conduit 12 and/or transmit electromagnetic radiation from the conduit 12 to a receiver (not shown), a carriage 16 for moving second waveguides 22b, 24b of the wave coupling between a deployed condition and retracted condition and a pressure modifier 16 arranged in fluid communication with the conduit 12, the pressure modifier 16 being operable to change the pressure within the conduit 12.

The elongate conduit 12 has a first opening 12a and a second opening 12b. The openings 12a, 12b are spaced from one another at opposite ends of the conduit 12. The conduit 12 is hollow so as to define a fluid passageway between the openings 12a, 12b such that the openings 12a, 12b are in exclusive fluid communication with one another via the conduit 12. A proximal end of the conduit 12 is connected to the body of a syringe 14 so as to provide a fluid-tight coupling therewith via the first opening 12a. A distal end of the conduit 12 defines a tip which is arranged and configured to enable the conduit to pierce human tissue or the like. For example, the conduit tip may define a sharp point such as that of a hypodermic needle; alternatively, it may be arranged to fit inside a disposable needle arranged to pierce tissue or the like. The second opening 12a is located at the tip of the conduit 12. The conduit 12 is formed of a resilient material such as steel. The conduit 12 may have an outer diameter which is less than 2 mm, 1.5 mm or less than 1 mm. Preferably, the conduit has an outer diameter which is equal to or less than 0.95 mm. In some embodiments the conduit may comprise a conventional hypodermic needle, such as a 20 gauge needle. The conduit 12 may have any suitable length, such as less than or equal to: 300 mm, 200 mm or 100 mm.

The wave coupling 18, 20, 22a, 22b, 24a, 24b in the illustrated embodiment is an optical coupling and comprises a plurality of first optical fibres 22a, 24a in a body portion of the probe 10 which are arranged to be aligned for signal communication with a plurality of second optical fibres 22b, 24b in a tip portion of the probe 10. Laser light may be transmitted from a laser (not shown) into an excitation fibre 22a of the first optical fibres 22a, 24a and then via a first light manipulation module 18. Light exiting the first light manipulation module 18 passes across a body/tip interface 17 (see FIG. 1b) to an excitation fibre 22b of the second optical fibres, via which the manipulated laser light may be directed into the conduit to a sample to be tested, such as tissue or fluid. A plurality of second collection fibres 24b (only one is shown for clarity) collect light from the sample and transmit the light back across the body/tip interface 17 to a second light manipulation module 20 arranged to manipulate the light returned from the sample and pass the output light to a plurality of first collection fibres 24a via which light exiting the second light manipulation stage 20 may be transmitted to a receiver, such as a spectrometer.

As will be appreciated, the exact configuration of the wave coupling according to embodiments of the invention will depend on factors such as the type of electromagnetic radiation used, the target sample and the type of receiver used. In embodiments of the invention the wave coupling may comprise any suitable waveguides and manipulation modules.

In the illustrated embodiment, the set of second optical fibres consists of a single excitation optical fibre 22b and six collection optical fibres 24b, which can be connected to one another to improve the stiffness of the second waveguides 22b, 24b. The close proximity of the optical fibres 22b, 24b forming the second waveguides 22b, 24b may provide for particularly efficient collection of light from the sample, such as Raman scattered light. While only a single excitation optical fibre 22b and six collection optical fibres 24b are provided, there may in other embodiments be a plurality of either. The second waveguides 22b, 24b, or components thereof, may be clad with a metal coating or jacket to improve the stiffness of the second waveguides 22b, 24b. The tip 22c, 24c of each optical fibre may be configured to provide a substantial overlap between the illuminating cone and the collection cones.

In the illustrated embodiment, the optional carriage 16 for moving the second optical fibres 22b, 24b between the deployed and retracted conditions comprises a plunger 16 of the syringe 14. The plunger 16 is conventional in that it has a body 16b having a piston seal 16a at one end which is contained within the barrel 15 of the syringe 14 and an enlarged base 16c which protrudes from the barrel 15 of the syringe 14 and may be used to actuate the plunger 16. The light manipulation modules 18, 20 are mounted on the plunger body 16b on the body side of the coupling interface 17. Consequently, movement of the plunger 16 causes corresponding movement of the second optical fibres 22b, 24b.

The syringe 15 defines a pressure modifier arranged in exclusive fluid communication with the first opening 12a of the conduit 12, the pressure modifier being operable to change the pressure at the first opening 12a of the conduit 12. Thus, a probe 10 according to such an embodiment includes a pressure modifier which can be used to modify the pressure within the conduit 12 to draw fluid or cells into the conduit 12 or expel fluid from the conduit 12. In embodiments where a tip, or other portion, of the second optical fibres 22b, 24b are arranged to be moved to the second opening 12b, it is advantageous to be able to expel fluid, such as saline solution, from the conduit 12 because this may clear the passageway between the tip of the second optical fibres 22b, 24b and the target tissue of subcutaneous tissue and/or fluid that may inhibit the passage of electromagnetic radiation. In some embodiments the optical coupling between the probe and tissue may also be improved. In embodiments where fluid is to be tested (as described in more detail with reference to FIG. 4), it is advantageous to be able to draw the test fluid into the conduit 12. Thus, the probe 10 according to the illustrated embodiment conveniently makes use of a syringe plunger 16 to act as the pressure modifier and carriage. The tip portion of the syringe 15 provides a convenient structure to which to attach the conduit.

In other embodiments which include a carriage for moving one or more portions of the wave coupling, the carriage may be any suitable part arranged to move relative to the conduit of the probe and should the embodiment also include a pressure modifier, the carriage need not also serve as the pressure modifier. For example, the plunger 16 of the illustrated embodiment may include an opening, or one way valve, through the piston seal 16a such that the plunger can be depressed without forcing fluid into the conduit 12. Although the plunger of such an embodiment may affect the pressure within the conduit 12, it is not arranged to modify the pressure in the conduit such that a substantial quantity of fluid can be drawn into, or purged from, the conduit and thus is not considered to be a pressure modifier as disclosed herein. A substantial quantity in embodiments of the invention may be at least 5%, 10%, 20%, 30%, 40%, 50%, 75% or 100% of the volume of the conduit chamber 12d.

In other embodiments which include a pressure modifier arranged to change the pressure within the conduit 12, the pressure modifier may be any suitable part arranged to increase or decrease the pressure at an opening of the probe 12. Should an embodiment include a carriage and a pressure modifier, the pressure modifier need not also serve as the carriage. For example, the optical coupling may be coupled to the syringe body of the illustrated embodiment and the plunger 16 may move relative to both the syringe body and optical coupling as is the case with the embodiment described with reference to FIG. 4. In some embodiments the pressure modifier may comprise a pump.

Figure 3:
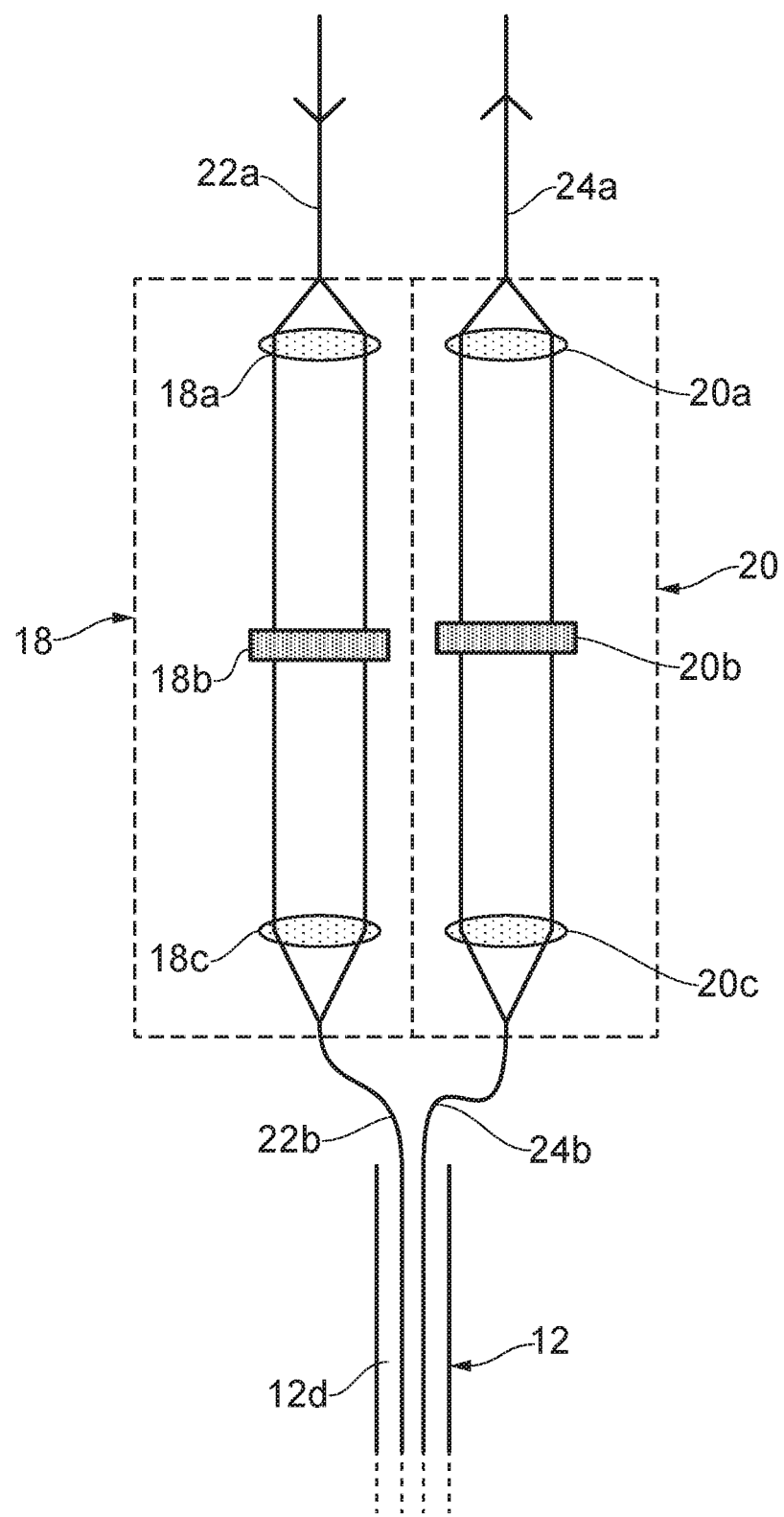

Referring additionally to FIG. 3, the light manipulation modules 18, 20 are shown in more detail. For clarity, as with FIG. 1c, only a single collection path 24a, 24b is shown.

The excitation or input optical fibre 22a, which in this embodiment is arranged to be coupled to a laser light source, directs laser light into a gradient index (GRIN) input lens 18a. The input lens 18a collimates the laser light to generate a collimated beam. The collimated beam is then passed through a short wavelength pass filter 18b that rejects Raman and photoluminescence emission generated within the input optical fibre 22a. The filtered light is then passed to a GRIN focussing lens 18c. The focussing lens 18c focusses the filtered light into the excitation optical fibre 22b which transmits the filtered light into the conduit 12 to the target sample.

Light from the sample is collected and collimated by a GRIN collecting lens 20c and directed to a long wavelength pass filter 20b that rejects the laser excitation light. Stokes shifted wavelengths are transmitted by the filter 20b. The filtered light is then focussed by a GRIN output lens 20a into the output optical fibre 24a which is arranged to be coupled to a receiver, such as a spectrometer for generating a Raman spectrum.

In other embodiments, any suitable electromagnetic radiation may be used as the excitation signal. It should be also noted that, while GRIN lenses have been described, any suitable lens type may be used in the optical coupling of other embodiments.

In the illustrated embodiment, the tips 22c, 24c of the second optical fibres 22b, 24b are closer to the second opening 12b of the conduit 12 when the second optical fibres 22b, 24b are in the deployed condition than when second optical fibres 22b, 24b are in the retracted condition. Thus, the probe 10 enables the position the tips 22c, 24c of the second optical fibres 22b, 24b to be varied. As such, the tips 22c, 24c may be stowed within the conduit 12 during insertion of the conduit 12 into human tissue or the like, so as to reduce the likelihood of the tips 22c, 24c being damaged or coming into contact with subcutaneous fluid or tissue which may otherwise impair the wave transmitting efficiency of the wave coupling. Once the conduit 12 has been inserted to a measurement depth, the second optical fibres 22b, 24b can be moved to the deployed condition for testing. When in the deployed condition, the tips 22c, 24c of the second optical fibres 22b, 24b may be in contact with the tissue sample.

Figure 1B:
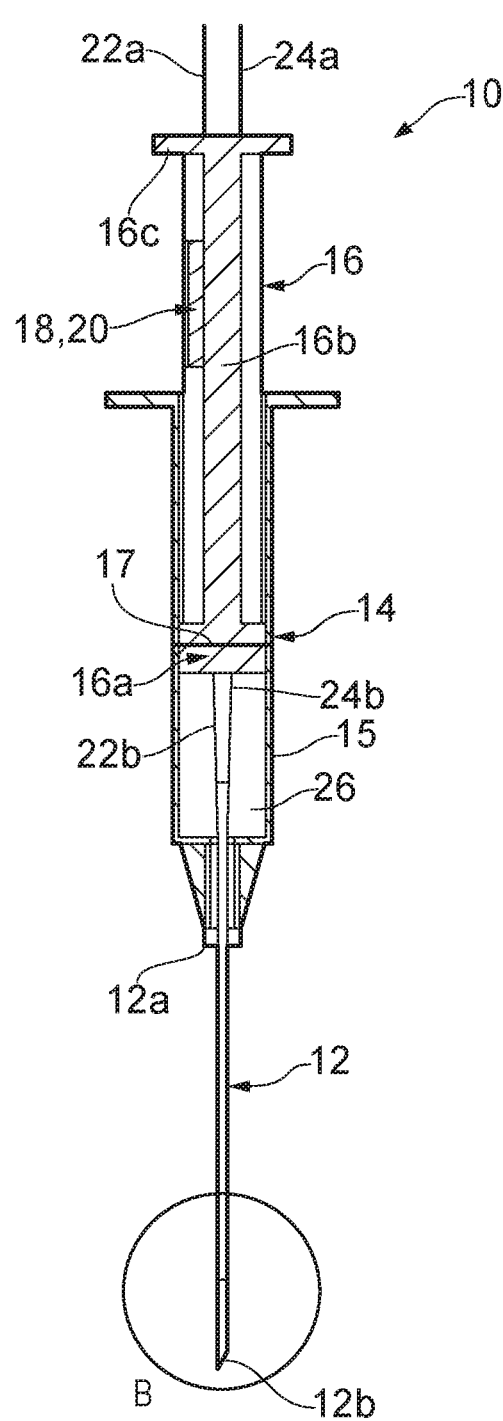
Figure 1C:
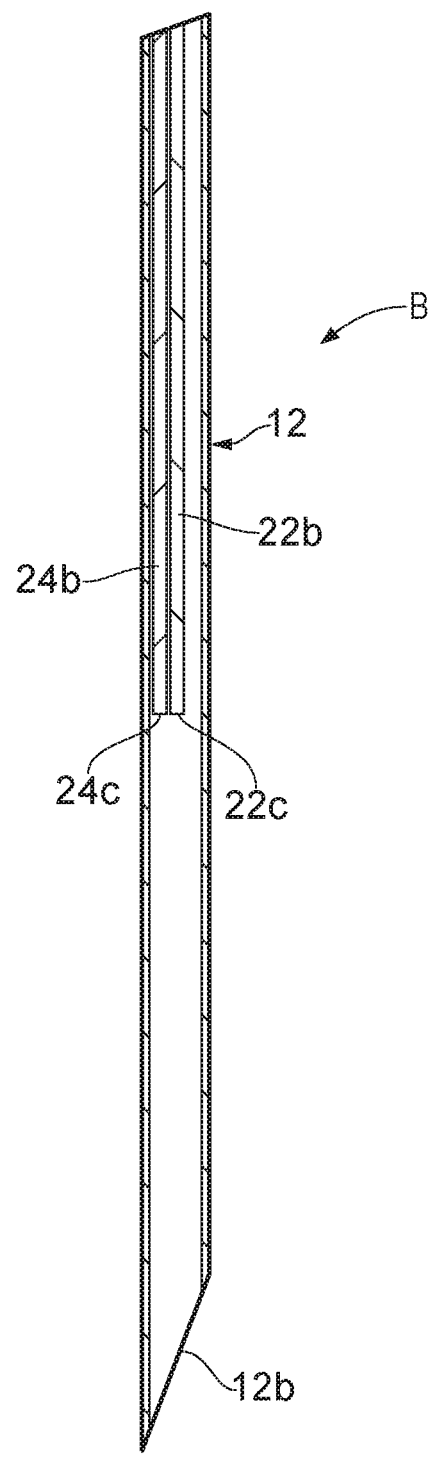
FIG. 1c is an enlarged view of the tip region B of the probe of FIG. 1b.

As shown in FIGS. 1b and 1c, the tips 22c, 24c of the second optical fibres 22b, 24b are spaced from second opening 12b of the conduit 12 when the second optical fibres 22b, 24b are in the retracted condition. For example, the tip 22c, 24c may be spaced from the second opening 12b by at least: one tenth of; one eighth of; one quarter of; a half of; three quarters of; or the entire length of the conduit 12. Thus, a probe 10 according to such an embodiment enables the tip 22c, 24c of the second optical fibres 22b, 24b to be spaced from the second opening 12b of the conduit 12. Increasing this spacing can provide a more efficient buffer between the second opening 12b and the tip 22c, 24c of the second optical fibres 22b, 24b. However, there may be a trade-off between providing a suitable buffer spacing and enabling the tip 22c, 24c to easily reach a target location, such as the second opening 12b of the conduit 12. In embodiments which include a pressure modifier, it may be desirable for the tips 22c, 24c of the second optical fibres 22b, 24b to be spaced from the second opening 12b of the conduit 12 by less than one quarter of the length of the conduit 12 so as to limit the volume of fluid that is displaced as the second optical fibres 22b, 24b moves between the retracted and deployed configurations.

Referring additionally to FIGS. 2a to 2c, the tips 22c, 24c of the second optical fibres 22b, 24b are positioned at the second opening 12b of the conduit 12 when the second optical fibres 22b, 24b are in the deployed condition. This enables the conduit 12 to be inserted into tissue to a required measurement depth and the tips 22c, 24c of the second optical fibres 22b, 24b brought close to the tissue to be sampled. This may improve the testing accuracy of the probe 10 relative to an embodiment where the tips 22c, 24c of the element 22b, 24b are significantly spaced from the target tissue because the wave coupling of the probe 10 transmits the electromagnetic radiation substantially all of the way to and from the target tissue. Arranging the probe such that the tip 22c, 24c of the second optical fibres contacts the tissue sample when in the deployed condition may advantageously remove the need for a lens at the tip and/or remove the need for setting a focal distance.

Figure 4:
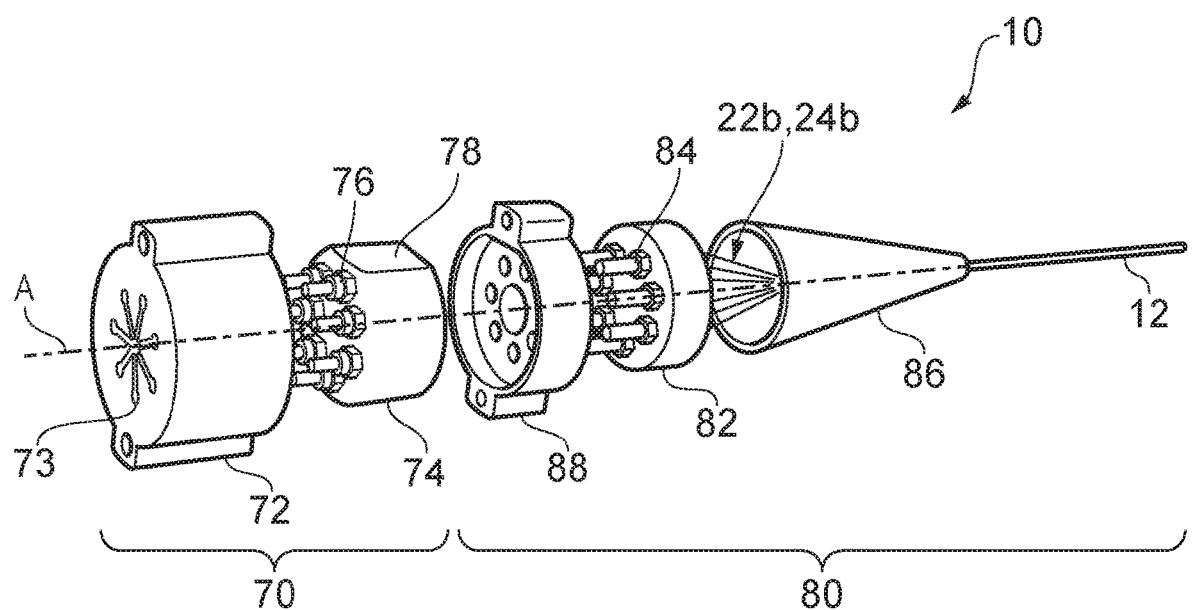
FIG. 4 a diagram of a probe according to a second embodiment of the invention, shown in an uncoupled condition.

FIG. 4 shows the disposable tip of the probe 10 in more detail. The probe 10 has a body portion 70 and a tip portion 80 that are arranged to be removably coupled to one another. Thus, the tip portion 80 may be disposed following a single use, but the body portion 70 can be reusable.

The body portion 70, of which only a part is shown in FIG. 4, houses the light manipulation modules (not shown) described with reference to FIG. 3. The light manipulation modules are arranged to be removably coupled to the second optical fibres 22b, 24b that are associated with the removable tip portion 80. The term "associated" is used to mean that second optical fibres 22b, 24b are part of the tip portion 80 rather than part of the body portion 70, such that following uncoupling of the portions 70, 80, the second optical fibres 22b, 24b remain coupled to the tip portion 80.

The tip portion 80 is arranged to be removably coupled to the body 70 by any suitable connectors; for example, one or more retention clips 92 such as flexible hooks or barbed structures arranged to mechanically engage with receiving apertures in the body, screw fittings, interference fit features or a magnetic coupling.

The set of first optical fibres 22a, 24a must be connected to and aligned with the set of second optical fibres 22b, 24b for the device 10 to function.

The tip portion 80 comprises a cylindrical mounting portion 82 which includes, in this embodiment, seven carrier holes arranged in an equiangular arrangement around the longitudinal axis A of the tip portion 80. Thus, the central axis of each carrier hole is separated from the central axes of adjacent carrier holes by around 51.4°. The first end of each second optical fibre is provided with a ferrule 84 arranged to project from an axial face of the mounting portion 82 when the fibre is mounted within one of the carrier holes. When the second optical fibres are mounted within the carrier holes, the second ends of the optical fibres extend from the mounting portion 82 into a conical tip 86 arranged to guide the fibres into the bore of the needle 12. The conical tip 86 can be secured to the mounting portion 82 by any suitable means, such as bonding or by way of a mechanical fixing.

The tip portion 80 further comprises a tip end fitting 88, via which the tip portion 80 is arranged to be coupled to the body portion 70. The end fitting 88 includes one or more holes which together are sized to receive the tip ferrules 84 when the end fitting 88 is coaxially coupled to the mounting portion 82. Ferrules 84 are inserted into standard ceramic mating sleeves to provide alignment of the waveguides. In this condition, the first ends of the second optical fibres are supported in the equiangular arrangement at the tip end fitting 88.

Similarly, the body portion 70 comprises a mounting portion 72 comprising a plurality of carrier holes 73, each first carrier being arranged to support a first optical fibre (not shown). The first carrier holes are disposed in the same equiangular arrangement around the longitudinal axis A.

The body portion 70 also comprises a body end fitting 74 at which sockets 76 located at first end regions of the first optical fibres are supported in the equiangular arrangement around the longitudinal axis A. The sockets 76 are arranged to receive the ferrules 84.

In the illustrated embodiment, the body end fitting 74 is provided with a keying surface 78 arranged to engage with corresponding keying surfaces on the mounting portion 72 and tip end fitting 88 to permit the tip portion 80 to be coupled to the body portion 70 in a single orientation. In other embodiments, any suitable arrangement can be provided to control the coupling orientation, such as male and female keying formations, magnetic poles, guide channels and rails, pin and socket arrangements and the like. In some embodiments, a marking may be provided to indicate the coupling orientation.

Various types of standard ferrules are available. Typically these could be 1 mm diameter stainless steel or 2.5 mm Ceramic. However, in other embodiments the ferrules may have any suitable size and be formed of any suitable material, such as a ceramic material, plastics material or stainless steel. The fibre may be inserted into the ferrule and cemented with an epoxy or adhesive, or connectors may also use crimped ferrules that do not require cement.

Figure 5:
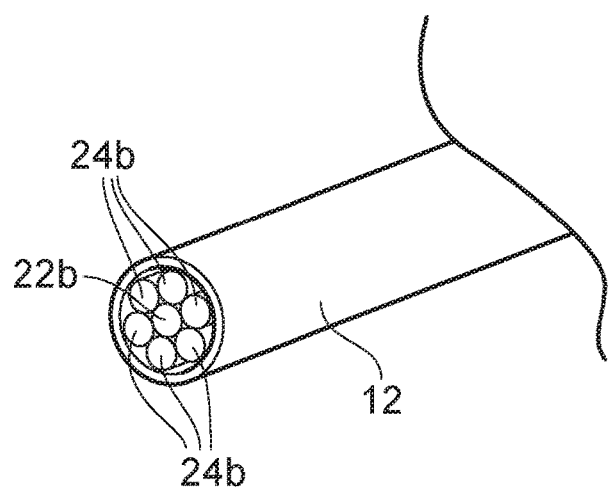
FIG. 5 is a diagram of the second waveguide tip arrangement.

Referring additionally to FIG. 5, it is preferred that the tip portion 80 has least four and preferably at least six second optical fibres 22b, 24b. The body portion 70 can comprise an equal number of first optical fibres 22a, 24a. A greater number of optical fibres increases light collection resulting in increased signal intensity and hence improved analytical performance. The diameter of each second optical fibres 22b, 24b is such that the tips of the second optical fibres 22b, 24b are housed within the bore of the needle 12 in a configuration in which the second excitation optical fibre 22a is central and surrounded by the second collection optical fibres 22b. This configuration enables the optical fibres to illuminate the sampling region evenly and in its entirety, so that scattered light is returned to all of the collection fibres 24b. This configuration can also avoid the collection of unwanted signal generated in the fibres themselves.

The tip portion 80 is arranged such that the orientation of the mounting portion 82 can be altered to control distribution of the fibres carrying laser light towards the sample and returning scattered light to the spectrometer. For example, this can be to ensure the central fibre 22b carries excitation laser light, and other fibres 24b return scattered light. Once the correct orientation is selected, the orientation of the mounting portion 82 is locked in place relative to the end fitting 88 to maintain this distribution.

As this alignment can be performed after the second fibres 22b, 24b have been mounted, ordering of the second fibres 22b, 24b in the tip is unimportant during construction, thus greatly lowering the complexity and cost of construction.

Figure 6:
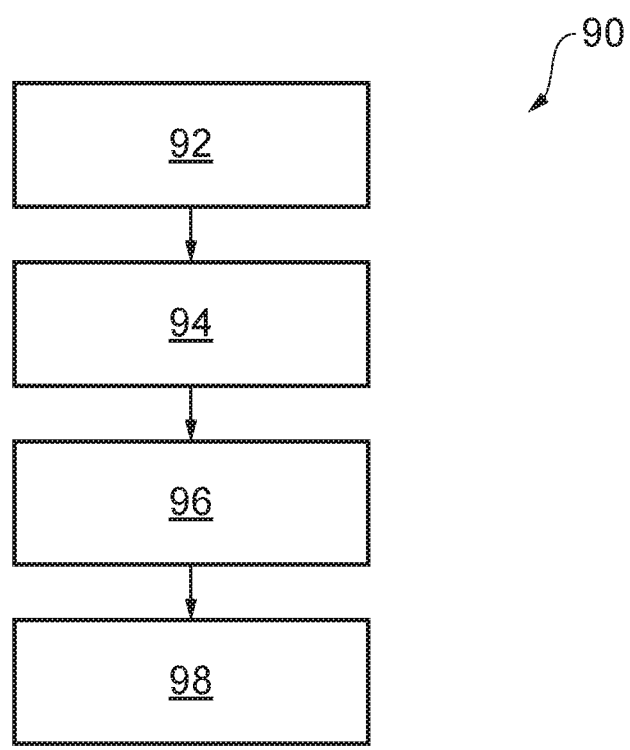
FIG. 6 is a flow chart illustrating a method according to an embodiment of the invention.

Referring additionally to FIG. 6, a method of manufacturing a tip portion 80 according to an embodiment of the invention is illustrated generally at 90.

At step 92 the ferrules 84 on the ends of the fibres 22b 24b protruding from the needle 12 are installed in carriers of the mounting portion 82.

At step 94, the central fibre 22b within the bore of the needle 12 can be identified using a microscope to view the needle end and an illumination source on each of the ferrules in turn until the central fibre 22b is identified.

At step 96, once identified, this fibre's ferrule 84 is placed in a known positioned hole in the end fitting 88, normally but not limited to, the hole next to the key formation.

At step 98, the mounting portion 82 is affixed to the end fitting 88 to maintain the orientation against the key. This keyed fibre is then used to maintain alignment with the fibre leading to the laser in the body portion 70 so that when the tip portion 80 is removed and replaced as an assembly, the excitation fibre remains in a constant position.

In any embodiment of the invention, the electromagnetic radiation may be within the range of ultraviolet to infrared.

In any embodiment of the invention including optical fibre, the fibre may have a diameter of 300 μm or less, preferably 200 μm or less and advantageously 150 μm or less.

Although the invention has been described above with reference to one or more preferred embodiments, it will be appreciated that various changes or modifications may be made without departing from the scope of the invention as defined in the appended claims. The word "comprising" can mean "including" or "consisting of" and therefore does not exclude the presence of elements or steps other than those listed in any claim or the specification as a whole. The mere fact that certain measures are recited in mutually different dependent claims does not indicate that a combination of these measures cannot be used to advantage.

What is claimed is:

1. A probe comprising:
    a body portion, the body portion comprising:
        a first mounting portion comprising a plurality of first carriers, each first carrier being arranged to support an elongate first waveguide, the first carriers being disposed in an equiangular arrangement around a longitudinal axis of the body portion;
        a plurality of first waveguides, each first waveguide being supported in a respective one of the plurality of first carriers; and
        a body end fitting at which first ends of the first waveguides are supported in the equiangular arrangement around the longitudinal axis of the body portion such that the first waveguides can transmit electromagnetic radiation signals from an energy source to the body end fitting and/or transmit electromagnetic radiation signals from the body end fitting to a receiver; and
    a tip portion arranged to be removably coupled to the body portion in a coaxial manner by one or more connectors, the tip portion comprising:
        a second mounting portion comprising a plurality of second carriers, each second carrier being arranged to support an elongate second waveguide, the second carriers being disposed in the equiangular arrangement around a longitudinal axis of the tip portion;
        a plurality of second waveguides, each second waveguide being supported in a respective one of the plurality of second carriers;
        a tip end fitting at which first ends of the second waveguides are supported in the equiangular arrangement around the longitudinal axis of the tip portion; and
        an elongate conduit, the elongate conduit having a first opening and a second opening, the first opening being coupled to the second mounting portion with the second waveguides extending from the second mounting portion into the elongate conduit such that, when the tip portion is coupled to the body portion and the first waveguides are axially aligned with the second waveguides, the second waveguides can transmit electromagnetic radiation signals from the first waveguides to the second opening of the elongate conduit and/or transmit electromagnetic radiation signals from the second opening of the elongate conduit to the first waveguides,
    wherein the second mounting portion and the tip end fitting are discrete components arranged to be coupled together during manufacture after the second mounting portion has been rotated about its axis to align a particular one of the second waveguides with a particular one of the first waveguides.

2. A probe according to claim 1, wherein the particular one of the first waveguides is a first excitation waveguide arranged to transmit electromagnetic radiation signals from the energy source to the body end fitting.

3. A probe according to claim 1, wherein the particular one of the second waveguides is a second excitation waveguide arranged to transmit electromagnetic radiation signals from the first excitation waveguide to the second opening of the elongate conduit.

4. A probe according to claim 1, wherein the remaining ones of the first and second waveguides are collection waveguides.

5. A probe according to claim 1, wherein the tip portion and body portion each define a cooperating keying formation arranged to permit the tip portion to be coupled to the body portion in just a single configuration.

6. A probe according to claim 1, wherein the tip portion comprises at least four second waveguides, the diameter of each second waveguide being such that the second ends of the second waveguides are housed within the bore of the elongate conduit in a configuration in which the second excitation waveguide is central and surrounded by the second collection waveguides.

7. A probe according to claim 1, wherein each waveguide comprises an optical fibre.

8. A probe according to claim 1, wherein the conduit comprises a hypodermic needle.

9. A probe according to claim 1, wherein the energy source comprises a laser light source.

10. A probe according to claim 1, wherein the second waveguides extend from the second mounting portion, through a conical tip and into the first end of the elongate conduit.

11. A probe according to claim 1, wherein the second waveguides are moveable relative to the elongate conduit in a direction parallel to the longitudinal axis of the tip portion such that the second waveguides have a retracted and a deployed position, the retracted position positioning the second wave guides such that a second end of each wave guide is spaced from the second end of the elongate conduit inside the elongate conduit by a first distance, and the deployed position positioning the second wave guides such that the second end of each wave guide is at a second distance which is relatively close to the second end of the elongate conduit in comparison to the first distance.

12. An optical spectroscope including a probe according to claim 1.

13. A probe tip portion arranged to be removably coupled to a probe body portion in a coaxial manner by one of more connectors, the body portion comprising: a first mounting portion comprising a plurality of first carriers, each first carrier being arranged to support an elongate first waveguide, the first carriers being disposed in an equiangular arrangement around a longitudinal axis of the body portion; a plurality of first waveguides, each first waveguide being supported in a respective one of the plurality of first carriers; and a body end fitting at which first ends of the first waveguides are supported in the equiangular arrangement around the longitudinal axis of the body portion such that the first waveguides can transmit electromagnetic radiation signals from an energy source to the body end fitting and/or transmit electromagnetic radiation signals from the body end fitting to a receiver, the tip portion comprising:
- a second mounting portion comprising a plurality of second carriers, each second carrier being arranged to support an elongate second waveguides, the second carriers being disposed in the equiangular arrangement around a longitudinal axis of the tip portion;
- a plurality of second waveguides, each second waveguide being supported in a respective one of the plurality of second carriers;
- a tip end fitting at which first ends of the second waveguides are supported in the equiangular arrangement around the longitudinal axis of the tip portion; and
- an elongate conduit for piercing human tissue, the elongate conduit having a first opening and a second opening, the first opening being coupled to the second mounting portion with the second waveguides extending from the second mounting portion into the elongate conduit such that, when the tip portion is coupled to the body portion and the first waveguides are axially aligned with the second waveguides, the second waveguides can transmit electromagnetic radiation signals from the first waveguides to the second opening of the elongate conduit and/or transmit electromagnetic radiation signals from the second opening of the elongate conduit to the first waveguides.

14. A method of assembling a tip portion of a probe according to any preceding claim, the method comprising the steps of:
- providing a tip portion comprising a second mounting portion, a tip end fitting and an elongate conduit, the second mounting portion comprising a plurality of second carriers, each second carrier being arranged to support an elongate second waveguide, the second carriers being disposed in an equiangular arrangement around a longitudinal axis of the tip portion;
- mounting a plurality of second waveguides in the second mounting portion, each second waveguide being supported in a respective one of the plurality of second carriers such that first ends of the second waveguides are supported in the equiangular arrangement around the longitudinal axis of the tip portion at a tip end fitting and second ends of the second waveguides extend from the second mounting portion into a first opening of the elongate conduit;
- rotating the second mounting portion to align a particular one of the second waveguides with a target position on the tip end fitting corresponding to the position of a first waveguide of a body portion such that, when the tip portion is coupled to the body portion and the second waveguides are axially aligned with the first waveguides, the second waveguides can transmit electromagnetic radiation signals from the first waveguides to the second opening of the elongate conduit and/or transmit electromagnetic radiation signals from the second opening of the elongate conduit to the first waveguides; and
- coupling the second mounting portion to the tip end fitting to inhibit relative rotation between them about the axis of the tip portion.

15. A method according to claim 14, comprising a step of:
prior to the step of rotating, identifying the particular one of the second waveguides by directing electromagnetic radiation down successive first ends and viewing the tip of the elongate conduit until the electromagnetic energy is registered at the second end of the particular one of the second waveguides.

16. A method according to claim 14, whereby the particular one of the second waveguides is an excitation waveguide and wherein the tip portion comprises at least four second waveguides, the diameter of each second waveguide being such that the second ends of the second waveguides are housed within the bore of the elongate conduit in a configuration in which the second excitation waveguide is central and surrounded by the second collection waveguides.

* * * * *